(12) United States Patent
Fukuda et al.

(10) Patent No.: US 10,088,467 B2
(45) Date of Patent: Oct. 2, 2018

(54) BLOOD TESTING APPARATUS AND BLOOD TESTING METHOD

(71) Applicant: NIHON KOHDEN CORPORATION, Tokyo (JP)

(72) Inventors: Hiroyuki Fukuda, Tokyo (JP); Yoshihiro Niiyama, Tokyo (JP); Fumihiko Murayama, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 327 days.

(21) Appl. No.: 14/643,067

(22) Filed: Mar. 10, 2015

(65) Prior Publication Data

US 2015/0268221 A1    Sep. 24, 2015

(30) Foreign Application Priority Data

Mar. 18, 2014  (JP) ................................. 2014-055479

(51) Int. Cl.
*G01N 33/487* (2006.01)
*G01N 33/49* (2006.01)
*G01N 35/10* (2006.01)

(52) U.S. Cl.
CPC ....... *G01N 33/48792* (2013.01); *G01N 33/49* (2013.01); *G01N 35/10* (2013.01)

(58) Field of Classification Search
CPC ... G01N 33/48792; G01N 35/10; G01N 33/49
USPC ......... 73/61.65, 61.68; 422/68.1, 73; 436/70
See application file for complete search history.

(56) References Cited

U.S. PATENT DOCUMENTS

| 6,632,679 B1 | 10/2003 | Breda |
| 2002/0085952 A1* | 7/2002 | Ellingboe ........... A61M 1/3621 422/45 |
| 2003/0003522 A1 | 1/2003 | Goldman |
| 2004/0065143 A1 | 4/2004 | Husher |
| 2005/0130236 A1 | 6/2005 | Goldman |
| 2006/0288760 A1 | 12/2006 | Duic |
| 2008/0206241 A1* | 8/2008 | Bebbington ......... A61K 31/505 424/133.1 |
| 2009/0120157 A1 | 5/2009 | Ciotti et al. |
| 2009/0142844 A1 | 6/2009 | Le Comte |

(Continued)

FOREIGN PATENT DOCUMENTS

| CN | 1135258 A | 11/1996 |
| CN | 1653323 A | 8/2005 |

(Continued)

OTHER PUBLICATIONS

Communication dated Aug. 26, 2015 issued by European Patent Office in counterpart European Patent Application No. 15158213.7.

(Continued)

*Primary Examiner* — R. A. Smith
*Assistant Examiner* — John M Royston
(74) *Attorney, Agent, or Firm* — Sughrue Mion, PLLC (57) ABSTRACT

A blood testing apparatus includes a blood acquiring section that acquires a blood sample, a particle counter that measures a particle count in the blood sample, and an erythrocyte sedimentation rate (ESR) measuring section that measures a erythrocyte sedimentation rate in the blood sample. The particle counter and the ESR measuring section being arranged in parallel.

17 Claims, 5 Drawing Sheets

(56) References Cited

U.S. PATENT DOCUMENTS

2014/0020457 A1* 1/2014 Dayel .................... G01N 15/05
73/61.68
2014/0341780 A1* 11/2014 Ishii ....................... G01N 33/49
422/73

FOREIGN PATENT DOCUMENTS

| CN | 1864060 A | 11/2006 |
|----|-----------|---------|
| CN | 101218493 A | 7/2008 |
| CN | 101228426 A | 7/2008 |
| JP | 9-505146 A | 5/1997 |
| JP | 2007-504468 A | 3/2007 |
| JP | 4648905 B2 | 3/2011 |
| WO | 95/14224 A1 | 5/1995 |

OTHER PUBLICATIONS

Communication dated Jun. 27, 2017, from the Japanese Patent Office in counterpart application No. 2014-055479.
Communication issued by the State Intellectual Property Office of P.R. China on Oct. 16, 2017, in counterpart Chinese Patent Application No. 201510106515.4.

\* cited by examiner

BLOOD TESTING APPARATUS AND BLOOD TESTING METHOD

CROSS REFERENCE TO RELATED APPLICATION

This application is based on Japanese Patent Applications No. 2014-055479 filed on Mar. 18, 2014, the contents of which are incorporated herein by reference.

BACKGROUND

The presently disclosed subject matter relates to a blood testing apparatus and a blood testing method.

As a method for clinical test of the erythrocyte sedimentation rate (ESR), the Westergren method has commonly used. In the ESR test by the Westergren method, first, blood collected from the patient is poured into a blood sedimentation tube. When time elapses, red blood cells (RBCs) settle downward, and blood plasma remains in the upper side. The distance in which the RBCs in the blood sedimentation tube settle corresponds to the length between the upper end of the blood plasma, and the boundary line between the blood plasma and the RBCs. The distance (mm) in which the RBCs settle during a predetermined time period (for example, two hours or one hour) is measured.

In the case where a blood test is to be performed in addition to an ESR test, the tests are performed by using testing apparatuses which are produced respectively as a blood cell counter apparatus and an ESR measuring apparatus. As a result, blood must be sampled for each of the tests, and therefore a large burden is imposed on the patient.

In this connection, Japanese Patent No. 4,648,905 discloses an integrated apparatus including both a blood cell counter apparatus and an ESR measuring apparatus. In the integrated apparatus, in order to enable blood cells to be counted after a measurement of the erythrocyte sedimentation rate is conducted on a blood sample, the ESR measuring apparatus and the blood cell counter apparatus are arranged in line. According to the configuration, a blood sample which has been once collected can be used in both the ESR measurement and the blood cell count.

However, the ESR measurement usually requires at least a measurement time which is longer several times than that of the blood cell count. In the integrated apparatus disclosed in Japanese Patent No. 4,648,905, the ESR measuring apparatus and the blood cell counter apparatus are arranged in line, and therefore the blood cell counter apparatus must wait for the ESR measurement by the ESR measuring apparatus to end.

Therefore, the integrated apparatus has a problem in that, in the case where the ESR and the number of blood cell are measured, it takes a long time to measure them.

SUMMARY

An object of the invention is to provide a blood testing apparatus and a blood testing method in which the time required to measure the particle count and measure the ESR can be shortened.

The blood testing apparatus of the invention has a blood acquiring section, a particle counter, and an ESR measuring section. The blood acquiring section acquires a blood sample. The particle counter measures the particle count in the blood sample. The ESR measuring section measures the erythrocyte sedimentation rate in the blood sample. The particle counter and the ESR measuring section are arranged in parallel.

The blood testing method of the invention has steps of: acquiring a blood sample; distributing at least a part of the blood sample to a particle counter and an ESR measuring section; and measuring the particle count and erythrocyte sedimentation rate in the blood sample.

Furthermore, the blood testing method of the invention has steps of: acquiring a first blood sample; distributing at least a part of the first blood sample to a particle counter and an ESR measuring section; and measuring the particle count and erythrocyte sedimentation rate in the first blood sample, and, in the step of measuring the particle count and erythrocyte sedimentation rate in the first blood sample, during a period after the measurement of the particle count in the first blood sample is ended, and when the erythrocyte sedimentation rate in the first blood sample is measured, a second blood sample is acquired, at least a part of the second blood sample is distributed to the particle counter, and a particle count in the second blood sample is measured.

According to the invention, the particle counter and the ESR measuring section are arranged in parallel, and hence the same blood sample can be distributed for measuring the particle count and for measuring the ESR. As compared to the case where, after the ESR measurement, the measurement of the particle count is performed in line to the ESR measurement, while using the same blood sample, therefore, the time required to count blood cells and measure the ESR can be shortened. As a result, early screening of inflammatory disease can be performed.

DETAILED DESCRIPTION OF EMBODIMENTS

Hereinafter, embodiments of the blood testing apparatus and method of the invention will be described with reference to the accompanying drawings. In the figures, the identical components are denoted by the same reference numerals. In the drawings, the dimension ratios are exaggerated for the sake of convenience in description, and may be sometimes different from the actual ratios.

(First Embodiment)

<Outline of Blood Testing Apparatus>

Figure 1:
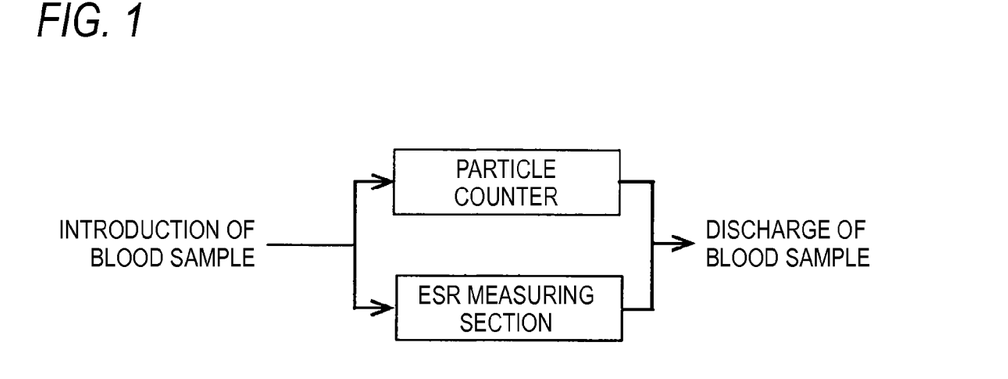
FIG. 1 is a conceptual view of a blood testing apparatus of a first embodiment of the invention.

As shown in FIG. 1, the blood testing apparatus can include a function of measuring the particle count, and that of measuring the ESR, and measuring sections are arranged in parallel. The blood testing apparatus acquires a blood sample of the test subject, distributes all or a part of the blood sample to a particle counter and an ESR measuring section, and measures the particle count and the ESR.

Figure 2:
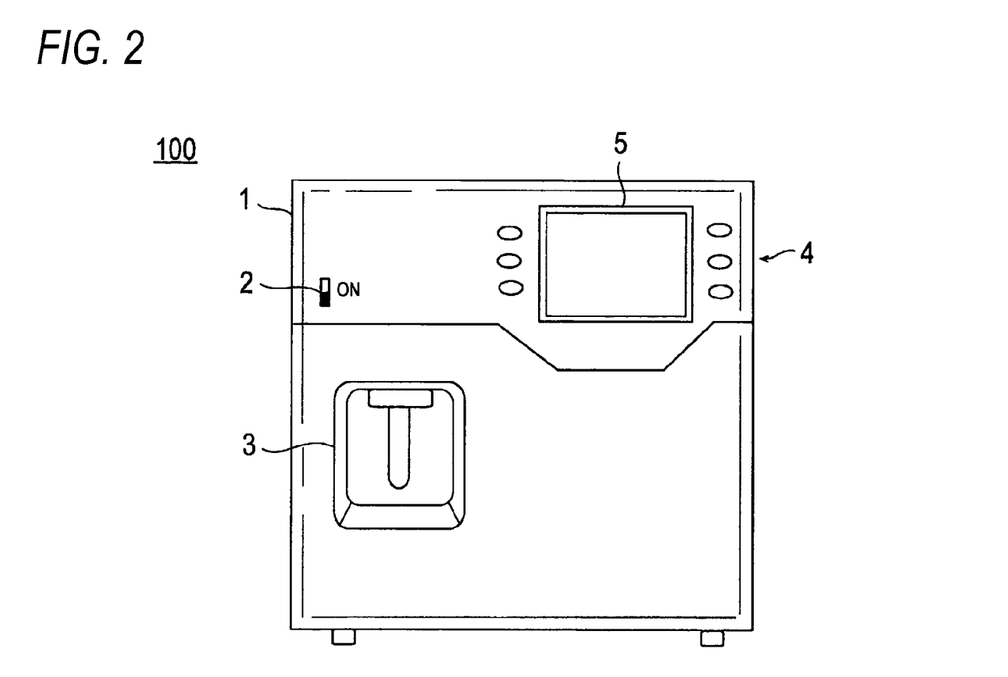
FIG. 2 is an external view of the blood testing apparatus of the first embodiment of the invention, as seen from the front side.

As shown in FIG. 2, the blood testing apparatus 100 can include a power supply switch 2, a blood collection tube receiving section 3, an operation panel 4, and a display panel 5 in a front portion of a housing 1. The power supply switch 2 turns ON/OFF the main power supply of the blood testing apparatus 100. When a medical person turns ON the power supply switch 2, the blood testing apparatus 100 is activated, and the blood sample in a blood collection tube is enabled to be tested.

The blood collection tube receiving section 3 is an introducing port through which, in the case where a blood sample in a blood collection tube is to be manually tested, the blood collection tube is introduced. When the medical person sets a blood collection tube into the blood collection tube receiving section 3, inputs settings through the operation panel 4, and performs operations for starting the measurement, measurements of the blood cells count and ESR in the blood sample in the blood collection tube are started. Results of the measurements are displayed on the display panel 5.

<Outline of Configuration of Blood Testing Apparatus>

Figure 3:
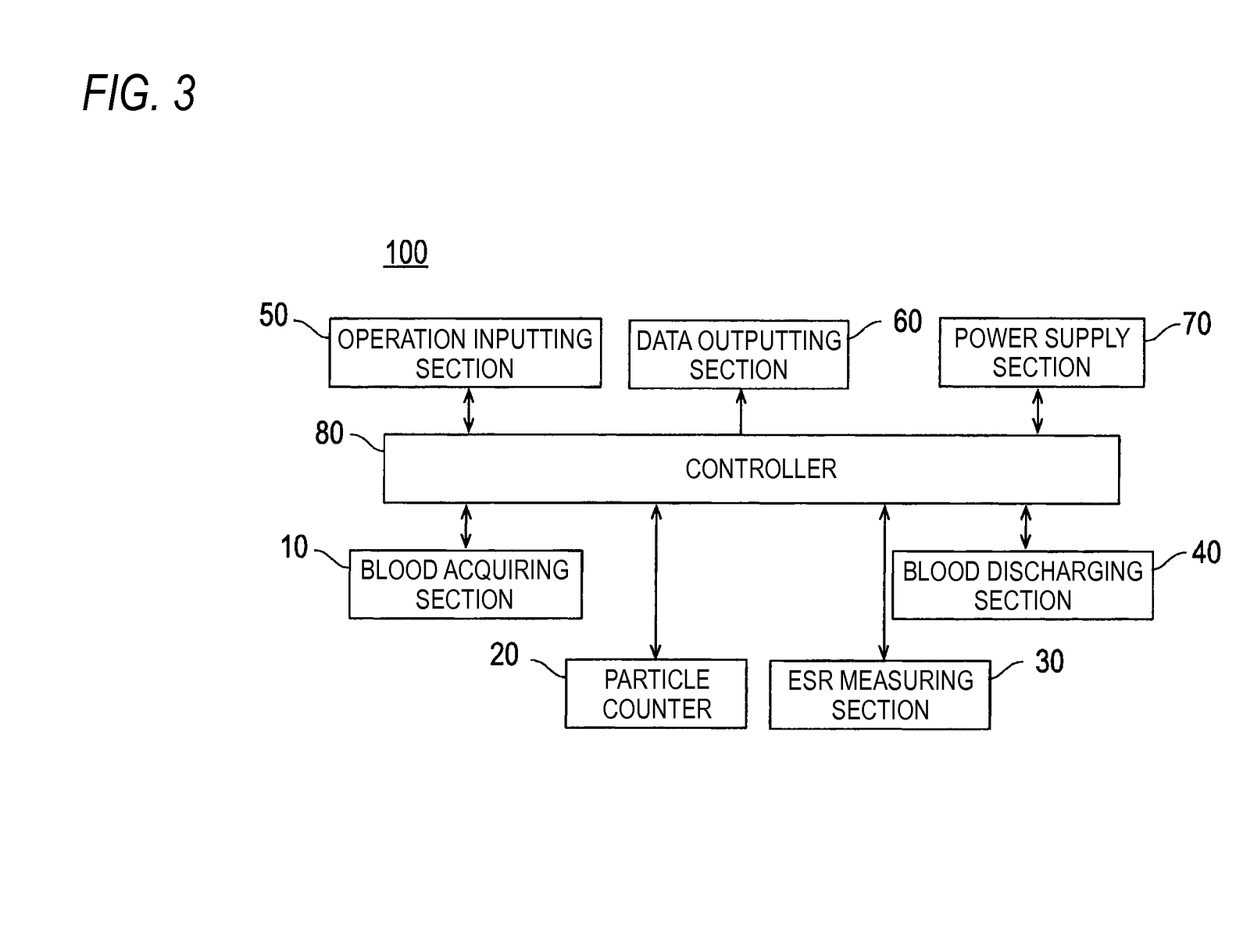
FIG. 3 is a block diagram schematically illustrating the configuration of the blood testing apparatus shown in FIG. 2.

As shown in FIG. 3, the blood testing apparatus 100 can include a blood acquiring section 10, a particle counter 20, an ESR measuring section 30, a blood discharging section 40, an operation inputting section 50, a data outputting section 60, a power supply section 70, and a controller 80. The blood acquiring section 10, the particle counter 20, the ESR measuring section 30, the blood discharging section 40, the operation inputting section 50, the data outputting section 60, and the power supply section 70 are electrically connected to the controller 80, and function in accordance with instructions from the controller 80. Hereinafter, the components of the blood testing apparatus 100 will be described with reference to FIGS. 4 and 5.

<Blood Acquiring Section>

Figure 4:
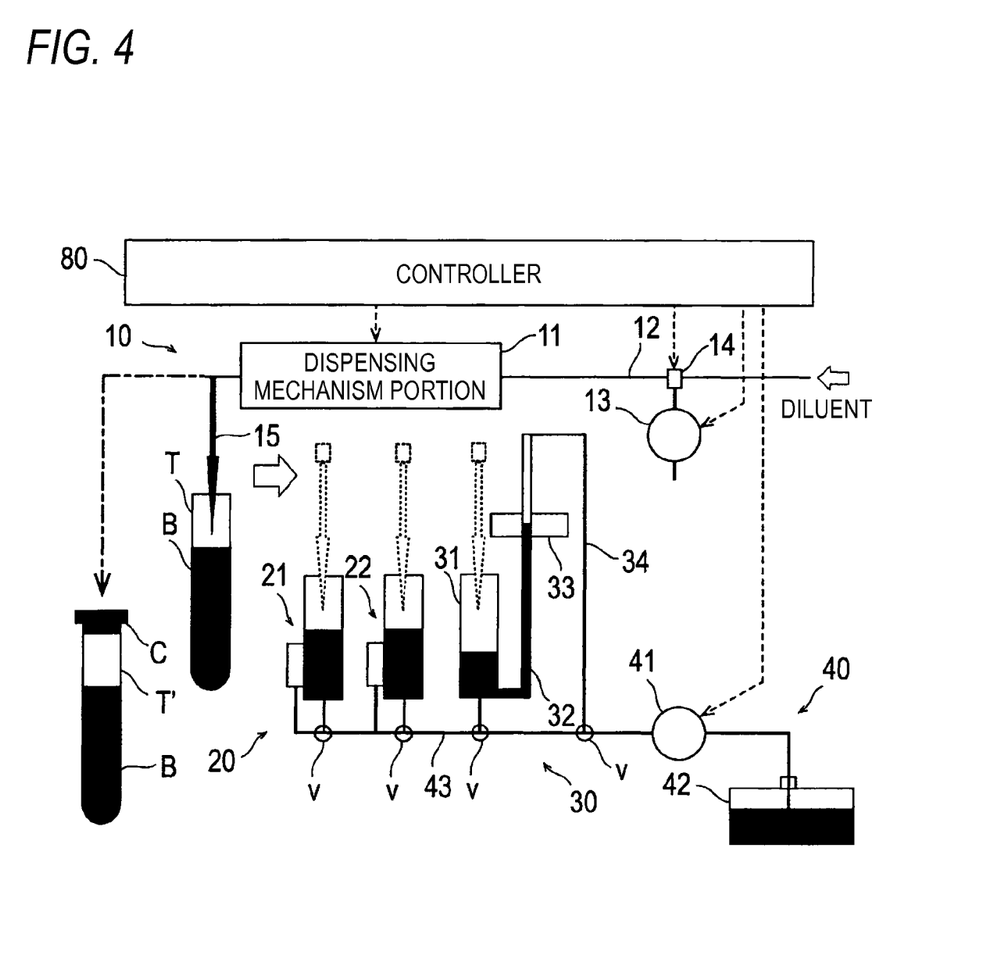
FIG. 4 is a diagram schematically illustrating the flow of a blood sample in the blood testing apparatus shown in FIG. 2.

The blood acquiring section 10 acquires a blood sample of the test subject, and distributes the blood sample to the particle counter 20 and the ESR measuring section 30. The blood acquiring section 10 can include the blood collection tube receiving section 3, a dispensing mechanism portion 11, a first pipe 12, a suction pump 13, an electromagnetic valve 14, and a nozzle 15.

The dispensing mechanism portion 11 is connected to the suction pump 13 and the nozzle 15 through the first pipe 12. A supply port for supplying a diluent for diluting the blood sample is disposed in one end portion of the first pipe 12.

The blood sample B is previously collected from the patient by the medical person, and contained in the blood collection tube T. As an anticoagulant, for example, EDTA is added into the blood collection tube T. Alternatively, the blood sample B may be contained in a blood collection tube T' having a cap C.

The dispensing mechanism portion 11 can include a moving mechanism which is not shown. The moving mechanism can include a function of moving the nozzle 15 in the X, Y, and Z axis directions of an orthogonal coordinate system, and, in accordance with instructions from the controller 80, move the nozzle 15 from the position above the blood collection tube T to a predetermined position which is above the particle counter 20 or the ESR measuring section 30. The predetermined position is a position where the blood sample B can be adequately injected from the nozzle 15 into the particle counter 20 or the ESR measuring section 30.

The blood sample B in the blood collection tube T is sucked by the suction pump 13, and held by the nozzle 15. The nozzle 15 is moved to the predetermined position which is above the particle counter 20 or the ESR measuring section 30, and then injects a predetermined amount of the blood sample B into the counter or the section.

The dispensing mechanism portion 11 may include a sample chamber portion in which the blood sample sucked from the blood collection tube T is to be accommodated. In this case, when the measurement is started, the blood sample B in the blood collection tube T is sucked by the suction pump 13, and then accommodated in the sample chamber portion through the nozzle 15. At this time, the electromagnetic valve 14 is controlled by the controller 80 so as to cause the blood sample B to flow from the blood collection tube T into the sample chamber portion. When the dispensing mechanism portion 11 includes the sample chamber portion as described above, a large amount of blood sample can be accommodated, and therefore it is possible to cope with, for example, the case where there are many test items and a large amount of blood sample is necessary.

Although not illustrated, the blood acquiring section 10 includes a mechanism for washing blood flow paths in the dispensing mechanism portion 11, the first pipe 12, the suction pump 13, the electromagnetic valve 14, and the nozzle 15. In the case such as where the next blood sample is to be introduced, the flow paths can be washed as required.

<Particle Counter>

The particle counter 20 measures the particle count in the blood sample B. The particle counter 20 can further measure blood cell count, red blood cell count, white cell count, hemoglobin concentration (HGB), the hematocrit value (HCT) and etc. The particle counter 20 can include a first and a second measuring units 21, 22. Each of the first and the second measuring units 21, 22 has a chamber and a detecting portion. The chamber holds the blood sample B which is injected through the nozzle 15. The detecting portion measures the particle count in the blood sample B.

In the embodiment, the blood sample B is injected into the chamber of the first measuring unit 21, diluted 200 times with the diluent, and hemolyzed with a hemolyzing agent. Thereafter, the number of white blood cells is measured. The blood sample B in the chamber of the second measuring unit 22 is diluted 40,000 times with the diluent, and RBCs are counted. The chambers are connected to the blood discharging section 40. When electromagnetic valves v are opened, used blood samples are discharged to the blood discharging section 40.

The measurement items of the blood cell count includes, for example, white blood cells (WBCs), red blood cells (RBCs), the hemoglobin concentration (HGB), the hematocrit value (HCT), the mean corpuscular volume (MCV), the mean corpuscular hemoglobin (MCH), the number of platelets (PLT), the lymphocyte percentage (LY %), the monocyte percentage (MO %), the granulocyte percentage (GR %), lymphocytes (LY), monocytes (MO), and granulocyte (GR). However, the measurement items are not limited to them. In the measurement items, for example, the numbers and sizes of blood cells are measured by the electric resistance method. The hemoglobin concentration is measured based on the measurement principle of the colorimetric method, and the hematocrit is measured from cell pulses by the cumulative pulse height method (calculated by an RBC histogram). The techniques of measuring the numbers of the blood cells have commonly been used, and therefore their description is omitted. The data of the blood cell measurement are transmitted to the controller 80.

<ESR Measuring Section>

The ESR measuring section 30 measures the ESR (erythrocyte sedimentation rate) of the blood sample B. The ESR measuring section 30 can include a chamber 31, an ESR measurement tube 32, an ESR detecting section 33, and a second pipe 34. The chamber 31 holds the blood sample B which is injected through the nozzle 15.

The ESR measurement tube 32 is also called a blood sedimentation tube, and a glass tube having a slender shape. The lower end of the tube communicates with the chamber 31, and the upper end is connected to a third pipe 43 through the second pipe 34. The blood sample B in the chamber 31 is sucked by a discharge pump 41 until the liquid level in the ESR measurement tube 32 reaches a predetermined height.

The ESR detecting section 33 estimates the sedimentation distance from a change of the light absorbance to measure the ESR of the blood sample B. The measurement time for the ESR is about five minutes. The measurement data of the ESR are transmitted to the controller 80. The chamber 31 is connected to the blood discharging section 40, and the used blood sample is discharged into the blood discharging section 40.

<Blood Discharging Section>

The blood discharging section 40 sucks the used blood sample, and stores the sucked sample. The blood discharging section 40 can include the discharge pump 41, a discharge tank 42, and the third pipe 43. The discharge pump 41 sucks the used blood sample from the particle counter 20 and the ESR measuring section 30. The discharge tank 42 stores the used blood sample which is sucked by the discharge pump 41.

<Operation Inputting Section>

The operation inputting section 50 receives instructions from the controller 80 and data inputs from the medical person such as test items which are to be tested by the blood testing apparatus 100 (hereinafter, such items are referred to as "order"). The input instructions and data are transmitted to the controller 80.

<Data Outputting Section>

The data outputting section 60 outputs measurement data of the blood cell count, those of ESR, a menu for setting various items, an operation menu, messages, and the like. The data outputting section 60 may include a connection terminal (for example, a USB port or a printer port) for an external printer for printing the measurement data of the blood cell count and the ESR, on a sheet.

In the embodiment, in accordance with the order, the data outputting section 60 displays measurement results of both the blood cell count and the ESR on the display panel 5. In the configuration where the hematocrit value and the ESR are juxtaposedly displayed on the display panel 5, when the ESR value obtained as a result of measurement is to be evaluated, particularly, the medical person can be promoted to consider the hematocrit value, and therefore screening is facilitated. In addition to the hematocrit value, the hemoglobin concentration, the number of white blood cells, and the like can be displayed on the display panel 5 simultaneously with the display of the ESR value. Therefore, the medical person can easily perform screening for a disease such as anemia, or that involving inflammation.

Based on the measured hematocrit value, alternatively, the data outputting section 60 may output information relating to the reliability or effectivity of the ESR value which is acquired in the measurement. In accordance with the hematocrit value, for example, a message indicating that there is a possibility that the ESR measurement is not properly performed, may be displayed on the display panel 5.

When the measured hematocrit value exceeds a predetermined threshold, the data outputting section 60 may output an alarm. The alarm can be an audible alarm such as a voice or a buzzer sound, or a visual alarm such as blinking of a lamp.

Based on the hematocrit value measured by the particle counter 20, the data outputting section 60 may correct the ESR value measured by the ESR measuring section 30, and output the corrected value.

<Power Supply Section>

The power supply section 70 supplies necessary electric power to the blood acquiring section 10, the particle counter 20, the ESR measuring section 30, the blood discharging section 40, the operation inputting section 50, the data outputting section 60, and the controller 80.

<Controller>

Figure 5:
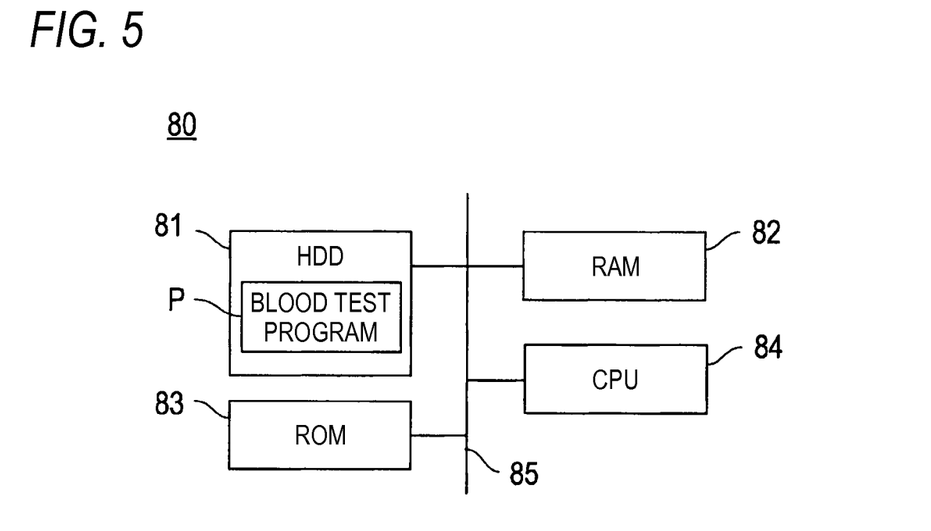
FIG. 5 is a block diagram schematically illustrating the configuration of a controller of the blood testing apparatus shown in FIG. 2.

The controller 80 controls the blood acquiring section 10, the particle counter 20, the ESR measuring section 30, the blood discharging section 40, the operation inputting section 50, the data outputting section 60, and the power supply section 70. As shown in FIG. 5, the controller 80 can include an HDD 81, a RAM 82, a ROM 83, and a CPU 84, and these components are communicably connected to one another by a bus 85. The HDD 81 is a hard disk drive which stores a blood test program P in the embodiment, various software programs for causing the blood test program P to operate, various data, and the like.

The blood test program P in the embodiment is configured so as to cause the blood testing apparatus 100 to execute the blood testing method. For example, the various data include basic data such as the ID, name, and age of the patient on whom blood sampling for a blood test was performed, and measurement data of the patient. A label on which the patient ID is printed is applied to the blood collection tube T. The blood collection tube T and the measurement data are managed according to the patient ID.

The RAM 82 is a volatile storage device, and temporarily stores the blood test program P, the test items, and the measurement data. The ROM 83 is a nonvolatile storage device, and stores various parameters which are used in execution of the blood test program P, and the like.

The CPU 84 is a processor which executes the blood test program P, and the various software programs for causing the blood test program P to operate.

As described above, the blood testing apparatus 100 has the configuration of acquiring the blood sample B of the test object, distributing at least a part of the blood sample B to the particle counter 20 and the ESR measuring section 30, and measuring the particle count and ESR in the blood sample B. The time required to measure the particle count is about 1 minute, and by contrast that required to measure the ESR is about 5 minutes. The time required to measure the ESR is longer than that required to measure the particle count.

In the embodiment, the particle counter 20 and the ESR measuring section 30 are arranged in parallel, and therefore the same blood sample B can be distributed as the sample for measuring the particle count, and also as that for measuring the ESR. As compared to the case where, after the ESR measurement, the measurement of the particle count is performed in line to the ESR measurement, while using the same blood sample B, therefore, the time required to perform one of the measurement of the particle count, and the ESR measurement, and that required to perform both the measurements in parallel can be shortened. As a result, early screening of inflammatory disease can be performed.

With respect to a blood sample relating to the order including the blood cell count test and the ESR test, the measurement of the ESR and the particle count can be performed in parallel. As a result, in the case where the ESR value acquired in the ESR measurement is to be corrected by using the hematocrit value acquired in the measurement of the particle count, the ESR value can be corrected immediately after the completion of the ESR measurement.

Moreover, the blood testing apparatus 100 can efficiently perform measurements by using the time difference between the times for measuring the ESR and the particle count. Specifically, the blood acquiring section 10 continuously acquires blood samples, and, during a period when the ESR measuring section 30 measures the ESR in a previously acquired blood sample, the particle counter 20 measures the particle count of the blood sample that is acquired following the previously acquired blood sample. Hereinafter, the blood testing method of the embodiment will be described with reference to FIG. 6.

<Blood Testing Method>

Figure 6:
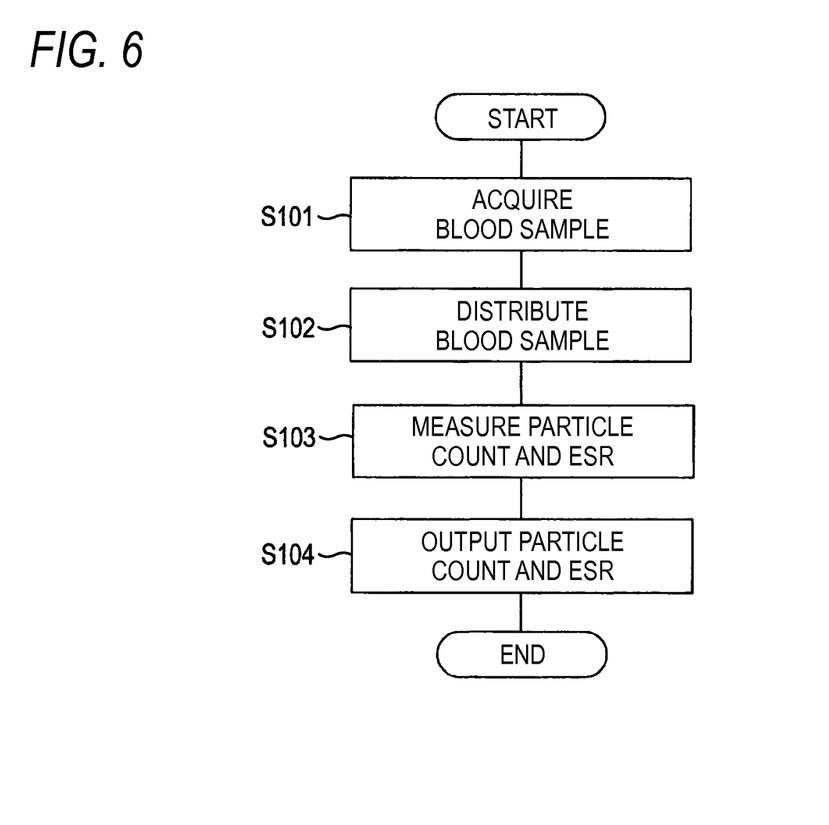
FIG. 6 is a flowchart illustrating the procedure of a blood testing method of the first embodiment of the invention.

FIG. 6 is a flowchart illustrating the procedure of the blood testing method of the first embodiment of the invention.

First, a blood sample is acquired (step S101). The medical person turns ON the power supply switch 2 to supply electric power to the blood testing apparatus 100. When the blood testing apparatus 100 is powered on, the CPU 84 of the controller 80 starts execution of the blood test program P. The medical person inputs the order through the operation panel 4 of the operation inputting section 50. The kind of the order can be selected for each of blood samples from a list of test items displayed on the display panel 5. Hereinafter, an example in which order for measuring "RBC", "WBC", "hematocrit", "hemoglobin concentration", and "ESR" are selected will be described. The input instructions are transmitted to the controller 80, and then stored in the RAM 82.

Then, the medical person sets the blood collection tube T which accommodates the blood sample B, into the blood collection tube receiving section 3, and operates the operation panel 4 to start the measurement.

When the measurement is started, the controller 80 moves the nozzle 15 of the blood acquiring section 10 to a position above the blood collection tube T, and starts the suction of the blood sample B in the blood collection tube T by the suction pump 13. The suction pump 13 applies a negative pressure to the blood sample B, and the sample is sucked into the nozzle 15. In accordance with instructions from the controller 80, at this time, the electromagnetic valve 14 is opened so as to allow the blood sample B to flow from the blood collection tube T toward the nozzle 15.

The amount of the blood sample B which is sucked from the blood collection tube T into the nozzle 15 can be changed in accordance with the amounts that are to be used in the particle counter 20 and the ESR measuring section 30. In the case of the measurement of the particle count, for example, the amount is about 50 µL, and, in the case of the ESR measurement, about 900 µL. When the suction of the blood sample B into the nozzle 15 is completed, the suction pump 13 is stopped, and the electromagnetic valve 14 is closed.

Next, the blood sample is distributed (step S102). In order to distribute the blood sample B to the ESR measuring section 30, the controller 80 moves the nozzle 15 toward the ESR measuring section 30. In the embodiment, the example in which the blood sample B is injected into the ESR measuring section 30, and then into the particle counter 20 will be described. However, the injection order of the blood sample B is not limited to this.

After the blood sample B in the blood collection tube T is sucked into the nozzle 15 by the suction pump 13, specifically, the controller 80 moves the nozzle 15 to a position above the chamber 31 of the ESR measuring section 30 in order to distribute the blood sample B to the ESR measuring section 30. Then, the electromagnetic valve 14 is opened, and a predetermined amount of the blood sample B is ejected into the chamber 31. Thereafter, the nozzle 15 is moved to a position immediately above the chamber of the first measuring unit 21 of the particle counter 20. The electromagnetic valve 14 is opened, the diluent is introduced into the first pipe 12, and the blood sample B is pushed by the diluent to be injected into the chamber. Moreover, the controller 80 causes the diluted blood sample in the chamber of the first measuring unit 21 to be sucked by the nozzle 15, further dilutes the diluted blood sample with the diluent, and then ejects the sample into the chamber of the second measuring unit 22.

Next, the particle count and the ESR are measured (step S103). In accordance with instructions from the controller 80, the particle counter 20 and the ESR measuring section 30 start the measurement. As described above, the embodiment has the structure in which the same blood sample is dispensed as a sample for measuring the particle count, and, on the other hand, also as that for measuring the ESR, and therefore the measurement of the particle count, and the ESR measurement can be performed in parallel. Furthermore, the embodiment has the structure in which the same blood sample is dispensed, and therefore measurements can be performed independently for respective test items. Namely, any one of the measurement of the particle count, and the ESR measurement can be independently performed.

As described above, with respect to a usual blood sample, the blood testing apparatus 100 of the embodiment functions as a blood cell counter apparatus, and, with respect to only a blood sample of a patient suspected of having inflammatory disease, can perform the ESR measurement which is time-consuming. As compared to the case where, after the ESR measurement, the measurement of the particle count is performed in line to the ESR measurement, while using the same blood sample, therefore, the time required for measurement can be shortened.

Moreover, the controller 80 controls the blood acquiring section 10 so that, when the measurement by the particle counter 20 and/or that by the ESR measuring section 30 are completed, the next blood sample is supplied. The particle counter 20 and the ESR measuring section 30 are arranged in parallel, and measurements are performed, whereby the measurement of the particle count for the next blood sample can be performed during the period when the ESR measurement requiring a longer time than the measurement of the particle count is performed. In the case where the blood acquiring section 10 acquires a second blood sample subsequently to a first blood sample, namely, the particle counter 20 can measure the particle count in the second blood sample subsequently to the first blood sample while the ESR measuring section 30 measures the ESR in the first blood sample.

Next, the particle count and the ESR are output (step S104). The controller 80 transmits the measurement data to the data outputting section 60, and instructs the section to output the measurement results. In accordance with instructions from the controller 80, the data outputting section 60 outputs the measurement results of the particle count and the ESR. For example, the data outputting section 60 displays the measurement results of red blood cells count, white blood cells count, the hematocrit value, the hemoglobin concentration, and the ESR on the display panel 5. In the embodiment, particularly, the data outputting section 60 juxtaposedly displays the hematocrit value and the ESR value on the display panel 5. When the medical person is to evaluate the ESR value obtained in the measurement, therefore, the medical person can be promoted to consider the hematocrit value, and consequently early screening of inflammatory disease can be easily performed.

(Second Embodiment)

Figure 7:
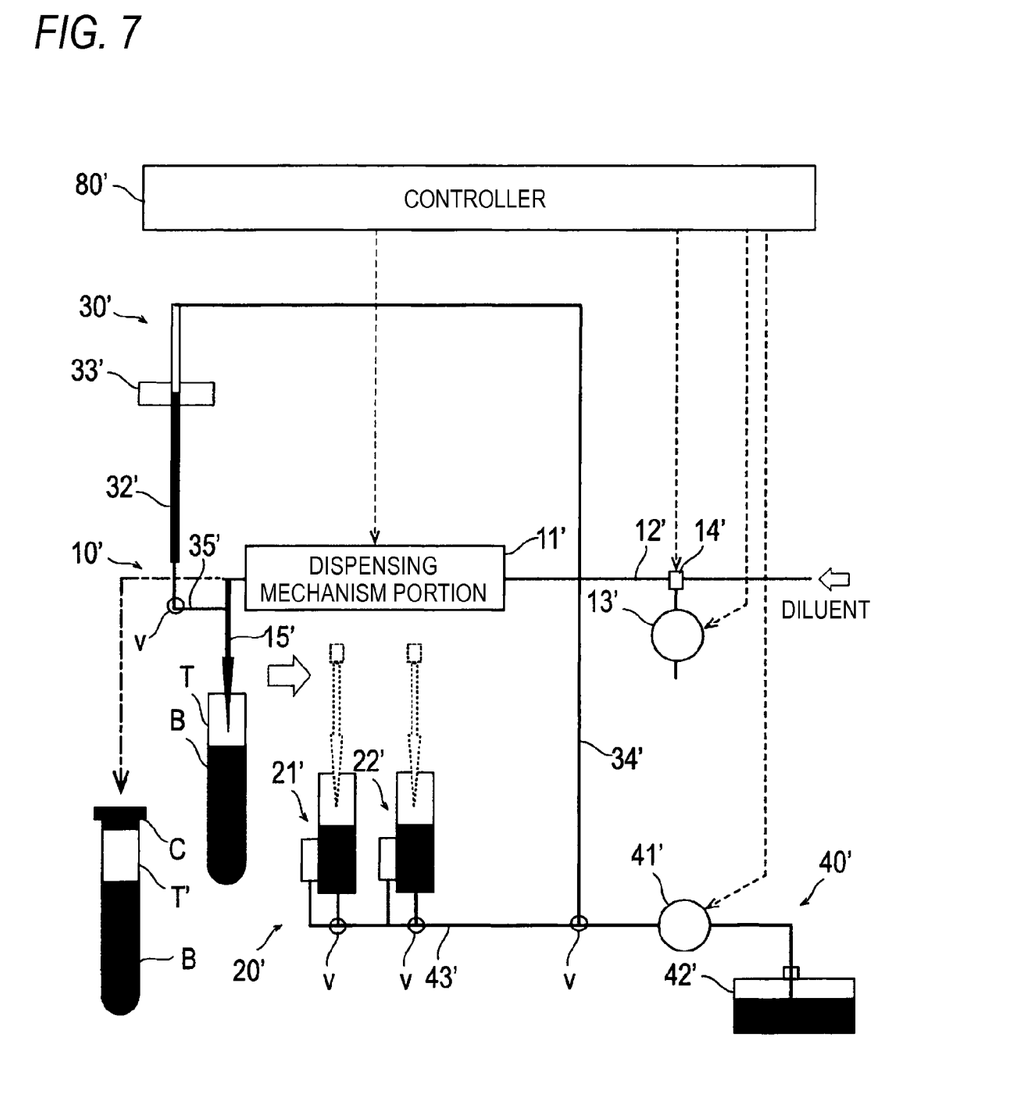
FIG. 7 is a diagram schematically showing the flow of a blood sample in a blood testing apparatus of a second embodiment of the invention.

As the first embodiment, the case where the nozzle is moved to a position above the ESR measuring section by moving mechanism, and the blood sample in the nozzle is distributed by injecting the sample into the ESR measuring section has been described. In a second embodiment, the lower end of a sedimentation measurement tube of an ESR measuring section is connected to a nozzle, and a blood sample is directly supplied from a blood collection tube to the ESR measuring section through the nozzle. In the following description of the second embodiment, with respect to the configuration which is identical with that of the first embodiment, its detailed description is omitted in order to avoid duplicate description.

FIG. 7 is a diagram schematically illustrating the flow of the blood sample in the blood testing apparatus of the second embodiment of the invention. An ESR measuring section 30' in the embodiment can include an ESR measurement tube 32', an ESR detecting section 33', a second pipe 34', and a fourth pipe 35'. Unlike the ESR measuring section 30 in the first embodiment, the ESR measuring section 30' in the second embodiment does not have a chamber. In the embodiment, the lower end of the ESR measurement tube 32' is connected to a nozzle 15' through the fourth pipe 35', and the upper end is connected to a third pipe 43' through the second pipe 34'. The blood sample B is directly supplied from the blood collection tube T to the ESR measurement tube 32' through the nozzle 15', and sucked by a discharge pump 41' of a blood discharging section 40' until the liquid level in the ESR measurement tube 32' reaches a predetermined height so that the sample can be used in the ESR measurement.

In the embodiment, the blood sample B is directly supplied from the blood collection tube T to the ESR measurement tube 32' through the nozzle 15', and therefore the time required for moving the nozzle 15' to a position above a chamber can be omitted. Since a chamber is not required in the ESR measuring section 30', the component cost can be reduced.

Although, in the above, the blood testing apparatus and the blood testing method have been described, it is a matter of course that those skilled in the art can adequately perform addition, modification, and omission within the scope of the technical concept of the invention.

As the first embodiment, for example, the configuration where the nozzle is moved to positions above the particle counter and the ESR measuring section, and the blood sample held by nozzle is distributed has been described. However, the invention is not limited to this configuration. For example, a configuration may be employed where the blood acquiring section has a pipe through which the nozzle is connected to the particle counter and the ESR measuring section, and an electromagnetic valve which controls the flow of a blood sample in the pipe, and the blood sample flowing through the pipe is controlled by opening/closing the electromagnetic valve so as to be distributed to the particle counter and the ESR measuring section.

In the first and second embodiments, the case has been described where the blood sample in the nozzle is pushed by the diluent which is introduced into the pipe connected to the dispensing mechanism portion, to be injected into the chamber. However, the method for introducing the diluent into the chamber is not limited to such a method. For example, a supply port for supplying the diluent may be disposed in each of the chambers, and the diluent may be supplied to the chamber through the supply port.

What is claimed is:

1. A blood testing apparatus comprising:
    a blood acquiring section that acquires a blood sample;
    a particle counter that measures a particle count in the blood sample; and
    an erythrocyte sedimentation rate (ESR) measuring section that measures a erythrocyte sedimentation rate in the blood sample,
    wherein the blood sample is supplied from the blood acquiring section in parallel to the particle counter and the ESR measuring section.

2. The blood testing apparatus according to claim 1 further comprising an outputting section which outputs together a measurement result of the particle count measured by the particle counter, and the erythrocyte sedimentation rate measured by the ESR measuring section.

3. The blood testing apparatus according to claim 2, wherein the outputting section further outputs information relating to a reliability or effectivity of the erythrocyte sedimentation rate which is measured by the ESR measuring section, based on a hematocrit value measured by the particle counter.

4. The blood testing apparatus according to claim 2, wherein the outputting section corrects the erythrocyte sedimentation rate which is measured by the ESR measuring section, based on a hematocrit value measured by the particle counter, and outputs the corrected rate.

5. The blood testing apparatus according to claim 3, wherein the outputting section further outputs an alarm in a case where the hematocrit value exceeds a predetermined threshold.

6. The blood testing apparatus according to claim 1, wherein the blood acquiring section comprises a sample chamber portion which accommodates the acquired blood sample, and
    at least a part of the blood sample accommodated in the sample chamber portion is distributed to the particle counter or the ESR measuring section.

7. The blood testing apparatus according to claim 1, wherein the blood acquiring section comprises:
    a nozzle which holds the acquired blood sample; and
    a pipe through which the acquired blood sample is directly supplied to the ESR measuring section,
    wherein the acquired blood sample is distributed to the ESR measuring section through the nozzle and the pipe, and the blood sample held by the nozzle is distributed to the particle counter.

8. A blood testing method performed using the blood testing apparatus of claim 1, the method comprising:
    acquiring a blood sample;
    distributing in parallel at least a part of the blood sample to a particle counter and an erythrocyte sedimentation rate (ESR) measuring section; and
    measuring a particle count and erythrocyte sedimentation rate in the blood sample.

9. A blood testing method performed using the blood testing apparatus of claim 1, the method comprising:
    acquiring a first blood sample;

distributing in parallel at least a part of the first blood sample to a particle counter and an ESR measuring section; and measuring a particle count and erythrocyte sedimentation rate in the first blood sample, and, wherein, in the measuring step, during a period after the measurement of the particle count in the first blood sample is ended and when the erythrocyte sedimentation rate in the first blood sample is measured, a second blood sample is acquired, at least a part of the second blood sample is distributed to the particle counter, and a particle count in the second blood sample is measured.

10. The blood testing method according to claim 8, further comprising outputting together a measurement result of the particle count measured by the particle counter, and the erythrocyte sedimentation rate measured by the ESR measuring section.

11. The blood testing method according to claim 9, further comprising outputting together a measurement result of the particle count measured by the particle counter, and the erythrocyte sedimentation rate measured by the ESR measuring section.

12. The blood testing method according to claim 10, wherein, in the outputting step, information relating to a reliability or effectivity of the erythrocyte sedimentation rate which is measured by the ESR measuring section is output based on a hematocrit value measured by the particle counter.

13. The blood testing method according to claim 11, wherein, in the outputting step, information relating to a reliability or effectivity of the erythrocyte sedimentation rate which is measured by the ESR measuring section is output based on a hematocrit value measured by the particle counter.

14. The blood testing method according to claim 10, wherein, in the outputting step, the erythrocyte sedimentation rate which is measured by the ESR measuring section is corrected based on a hematocrit value measured by the particle counter, and the corrected rate is output.

15. The blood testing method according to claim 11, wherein, in the outputting step, the erythrocyte sedimentation rate which is measured by the ESR measuring section is corrected based on a hematocrit value measured by the particle counter, and the corrected rate is output.

16. The blood testing method according to claim 12, wherein, in the outputting step, the erythrocyte sedimentation rate which is measured by the ESR measuring section is corrected based on a hematocrit value measured by the particle counter, and the corrected rate is output.

17. The blood testing method according to claim 13, wherein, in the outputting step, the erythrocyte sedimentation rate which is measured by the ESR measuring section is corrected based on a hematocrit value measured by the particle counter, and the corrected rate is output.

* * * * *